United States Patent [19]

Siegmund

[11] Patent Number: 5,571,015
[45] Date of Patent: Nov. 5, 1996

[54] DENTAL REPLACEMENT MOUNTING SYSTEM

[76] Inventor: Ernie Siegmund, 201-407 Graham Avenue, Winnipeg, Manitoba, Canada, R3C 0L3

[21] Appl. No.: 312,265

[22] Filed: Sep. 26, 1994

[51] Int. Cl.⁶ ..................................................... A61C 8/00
[52] U.S. Cl. .......................................................... 433/173
[58] Field of Search ................................. 433/173, 174, 433/175, 176

[56] References Cited

U.S. PATENT DOCUMENTS

| | | | |
|---|---|---|---|
| 3,732,621 | 5/1973 | Bostrom | 32/10 |
| 4,016,651 | 4/1977 | Kawahara | 32/10 |
| 4,178,686 | 12/1979 | Riess et al. | 433/201 |
| 4,713,006 | 12/1987 | Hakamatsuka et al. | 433/201 |
| 4,756,689 | 7/1988 | Lundgren et al. | 433/169 |
| 4,780,080 | 10/1988 | Haris | 433/174 |
| 4,988,297 | 1/1991 | Lazzara et al. | 433/173 |
| 5,015,186 | 5/1991 | Detsch | 433/173 |
| 5,030,095 | 7/1991 | Niznick | 433/174 |
| 5,069,622 | 12/1991 | Rangert et al. | 433/173 |
| 5,116,225 | 5/1992 | Riera | 433/173 |
| 5,145,372 | 9/1992 | Daftary | 433/173 |
| 5,281,140 | 1/1994 | Niznick | 433/173 |
| 5,350,301 | 9/1994 | De Buck | 433/173 |
| 5,417,569 | 5/1995 | Perisse | 433/173 |

*Primary Examiner*—Cary E. O'Connor
*Attorney, Agent, or Firm*—Andrus, Sceales, Starke & Sawall

[57] ABSTRACT

A system for mounting a dental prosthetic structure on a dental implant is disclosed which includes a mounting base for supporting the dental prosthetic structure, a transmucosal member for attachment to a dental implant and having an attachment portion for receiving the mounting base; and a fastener for affixing the mounting base to the transmucosal member. The mounting base has an end wall for supporting the dental prosthetic structure and a depending side wall engageable with the attachment portion of the transmucosal member. At least one of the transmucosal member and the mounting base is of angled configuration in longitudinal direction for supposing the respectively adjacent mounting base and prothetic structure at an angle to an axis of the implant for compensating implant angulation. The system is mountable on a conventional dental implant and provides a base to which a prosthetic structure such as a full or partial denture, a single tooth replacement, abutments therefor and an abutment mount can be mounted in complete alignment with adjacent teeth or abutments independent of the angulation of the associated dental implant.

10 Claims, 4 Drawing Sheets

DENTAL REPLACEMENT MOUNTING SYSTEM

BACKGROUND OF THE PRESENT INVENTION

The present invention relates to dental implants for tooth replacements such as crowns, bridges and dentures in the fields of dentistry, oral surgery and orthodontics and, more particularly, to a mounting system for selected directional support of a dental replacement.

A variety of dental replacement mounting arrangements and methods are known. One commonly used arrangement includes a dental implant in the form of a pin, screw, plate or solid or perforated cone which functions as an artificial dental root, a transmucosal member made of tissue compatible material which extends across the gingival tissue and is either integral with or affixed to the implant to provide a mounting base for an abutment for a dental prosthetic structure. All parts of these arrangements are provided with and interconnected by way of central axis boreholes and cooperating fasteners engageable therewith. Arrangements of this type are disclosed in U.S. Pat. No. 3,435,526 by Brancato, U.S. Pat. No. 4,016,651 by Kawahara et al., U.S. Pat. No. 4,178,686 by Riess et al., and U.S. Pat. No. 4,713,006 by Hakametsuka et al.

Attachment bases or implants for dental replacements are inserted or screwed into the jaw bone. However, since jaw bones are often rather narrow and are inclined in vertical direction and the attachment base must, for technical reasons, be well centred in the jaw bone, the longitudinal direction of the attachment base may not be in alignment with the longitudinal direction of adjacent teeth or abutments, because of the constructional restraints of central axis boreholes. This is a problem, since the teeth of the prosthetic structure should ideally align with the attachment base for maximum strength of the whole arrangement. The result is either a weak and unsatisfactory connection between the implant and the jaw bone or a misaligned prosthetic structure. Thus, a dental replacement arrangement is desired which would provide for compensation of a misalignment between the longitudinal direction of the implant and the longitudinal direction of adjacent teeth or abutments thereby ensuring that the prothetic structure is aligned with the attachment base.

Bostrom in U.S. Pat. No. 3,732,621 describes an implantable fixture for a dental prosthetic structure which fixture includes a first part for embedding into the jaw bone and a second part which serves as an attachment base for the prosthetic structure and passes through the weak tissue covering the bone tissue. The first and second parts are interconnected by way of a sealed ball and socket joint which can be locked in a desired angle or position. Thus, a misalignment of the implant with respect to the surrounding teeth can be compensated without misalignment of either the implant in the jaw bone or the prosthetic structure on the attachment base. However, the ball and socket joint may become unlocked when the prosthetic structure is subjected to biting stress or when the dental surgeon has to screw on the prosthetic structure. This can lead to misalignment of the attachment base. The misalignment can then only be corrected by removal of the prosthetic structure and resetting of the joint, which can be a serious problem if the prosthetic structure has already been permanently cemented onto the attachment base leaving the joint locking screw unaccessible.

Another attempt at solving the problem of angulation are angled abutments which are directly screwed into the implant and are commercially available, for example from CORE-VENT CORPORATION (Encino, Calif.). Although angled abutments can be used to compensate for angulation, they are unsuited for applications where lateral working space is restricted such as in single tooth replacement. The diameter of the circle, described by the abutment tip during screwing into the implant is frequently larger than the distance between adjacent teeth, making it impossible to use the angled abutment or forcing the dentist to use an abutment which does not fully compensate implant angulation. Thus, a tooth replacement mounting system is desired which fully compensates any implant angulation present and can be used in confined spaces.

SUMMARY OF THE PRESENT INVENTION

The above described problems with the prior art arrangements are now overcome with a mounting system in accordance with the invention which is mountable onto a conventional dental implant and provides a base to which a prosthetic structure such as a full or partial denture, a single tooth replacement, abutments therefor and an abutment mount can be mounted in complete alignment with adjacent teeth or abutments independent of the angulation of the associated dental implant.

Accordingly, the invention provides a system for mounting a dental prosthetic structure on a dental implant, which system includes a mounting base for supporting the dental prosthetic structure in a selected orientation, a transmucosal member for attachment to the dental implant and having an attachment portion for receiving the mounting base and fastening means for affixing the mounting base to the transmucosal member. The mounting base has an end wall for supporting the dental prosthetic structure and a depending side wall engageable with the attachment portion of the transmucosal member, wherein at least one of the mounting base and the transmucosal member is of angled configuration in longitudinal direction for supporting the respectively adjacent prosthetic a structure and mounting base at an angle to an axis of the implant.

This mounting system provides a multitude of possibilities for compensation of implant angulation. The transmucosal member may be constructed as an elbow having an upper section including the attachment portion which section extends at an angle to a lower section engageable with the implant. The angle of the elbow is preferably selected to compensate for implant angulation. If the upper and lower section of the transmucosal member are aligned with the implant axis when affixed thereto, implant angulation can be compensated in accordance with the invention with a mounting base of angled configuration. The end wall of the mounting base can be manufactured or machined to be at a sufficiently large angle to the side wall and, thus, the axis of the implant, once the base is installed on the transmucosal collar that the implant angulation is compensated. Furthermore, the top surface of the end wall which is adapted to support the dental prosthetic structure can be manufactured or machined at on angle to the side wall. Alternatively or additionally, an abutment mount can be permanently or removably affixed to the top surface of the mounting base in such a way that it will support an abutment at an angle to a longitudinal axis of the mounting base. Thus, it becomes apparent that the system in accordance with the invention provides a versatile multilevel angulation compensation arrangement which can be used even in very confined areas such as for single tooth replacements.

In a preferred embodiment, an abutment for a dental replacement is connected to the mounting base. The abutment is affixed to the mounting base by any of the means generally used in the field, such as soldering, casting, or screwing, and may have a different longitudinal orientation than the implant, transmucosal member and mounting base combination, which provides yet another way of compensating for misalignments between the implant and adjacent teeth or abutments. The mounting base is preferably cylindrical, but may also have a polygonal outer shape.

Instead of the abutment, the mounting base in another preferred embodiment is provided with a non-circular depression in its top surface, or with a trench which can be mated with a trench in the transmucosal member so that when a tooth replacement such as a crown is placed on the mounting base, the base and the transmucosal member are locked together against rotation. The transmucosal member is preferably a transmucosal collar which has an intermediate, radially outwardly directed, annular flange that divides the collar into a lower, non-circular portion for engagement with a socket of complementary shape in a top end of the implant and an upper, cylindrical attachment portion for engagement with the mounting base. The attachment portion is preferably threaded.

Prior art dental replacement arrangements employed vertical central axis fixation bore hole screws with the result that an artificial tooth affixed thereto always had the saute longitudinal orientation as the central access bore hole giving the restoration aesthetically unacceptable results. In contrast, the mounting system of this invention, which can be used in combination with conventional dental replacement components, allows the dental technician to fit an abutment thereto which is aligned with adjacent teeth or abutments and at an angle to the longitudinal orientation of the implant. This is achieved without sophisticated and expensive joints, which simplifies manufacture and installation and thereby reduces costs. Also, due to the lack of joints in the dental replacement system of the invention, there is no danger of misalignment of the supported tooth, bridge or denture during use by loosening and movement of the joint. Consequently, the mounting system in accordance with the invention provides a simple and cost efficient means for the making of angled dental replacement systems. When the mounting system of the invention is used in bridge restoration or denture fixation, diverse implant body angulations have no negative effect on perfect abutment parallelism so that an anatomically, structurally, functionally and hygienically correct restoration can be made.

BRIEF DESCRIPTION OF THE DRAWINGS

The invention will now be further described by way of example only and with reference to the accompanying drawings, wherein.

DESCRIPTION OF THE ILLUSTRATED EMBODIMENT

Figure 1:
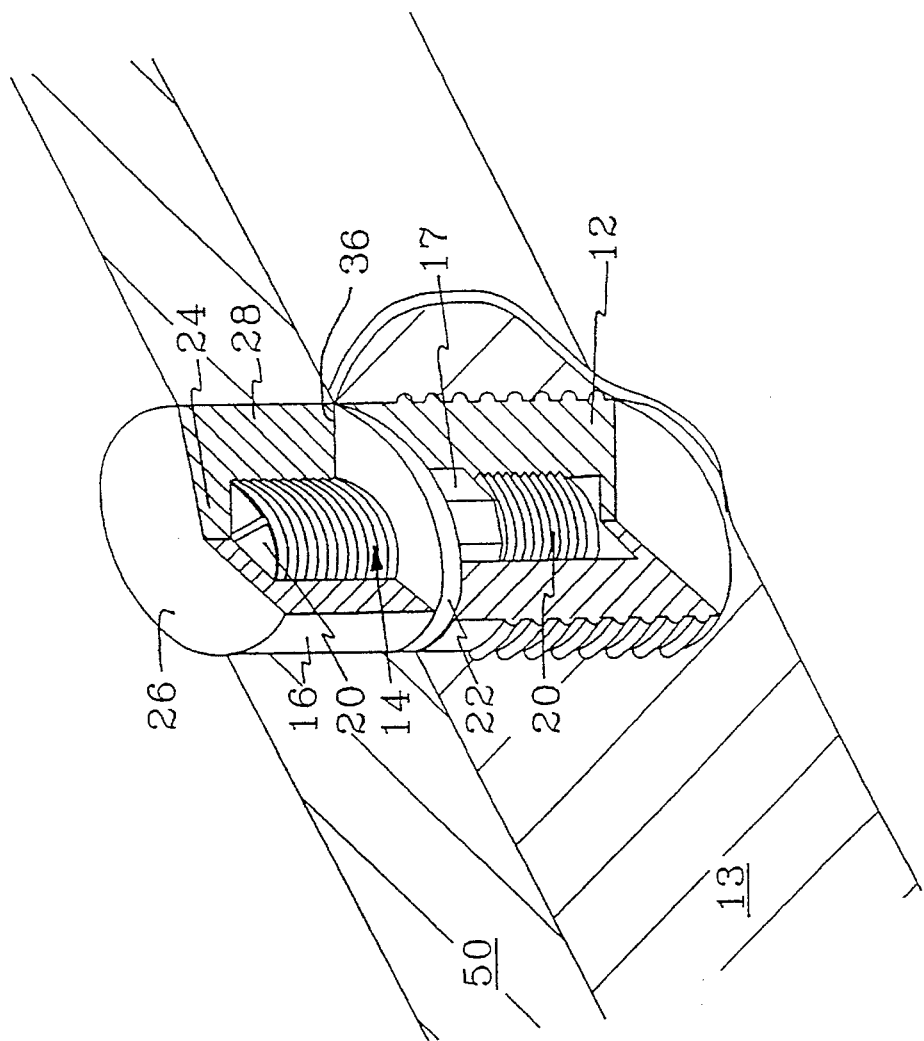
FIG. 1 is an isometric view of a preferred dental replacement mounting system in accordance with the invention in the installed condition, wherein the mounting base is of an angled configuration.
Figure 2:
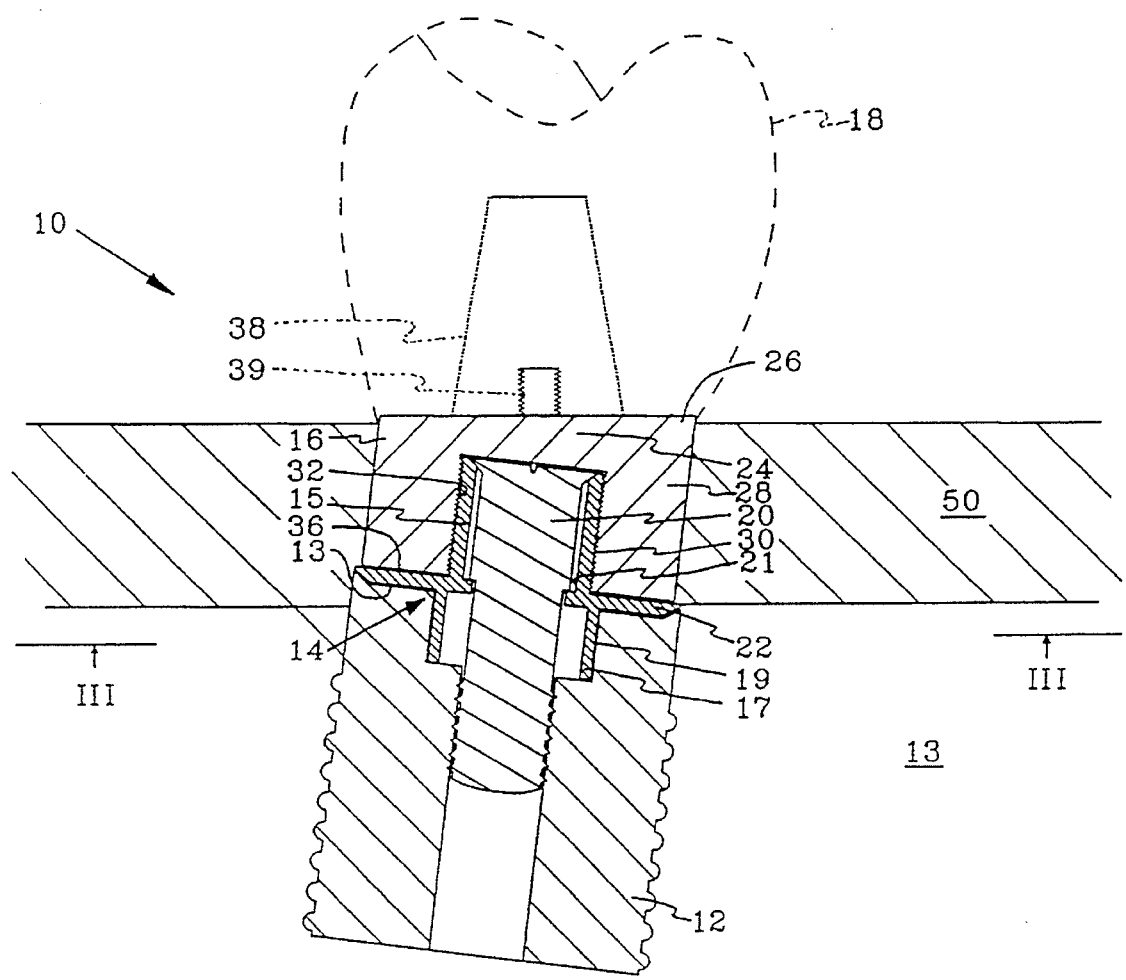
FIG. 2 is a longitudinal cross section through the embodiment shown in FIG. 1.
Figure 3:
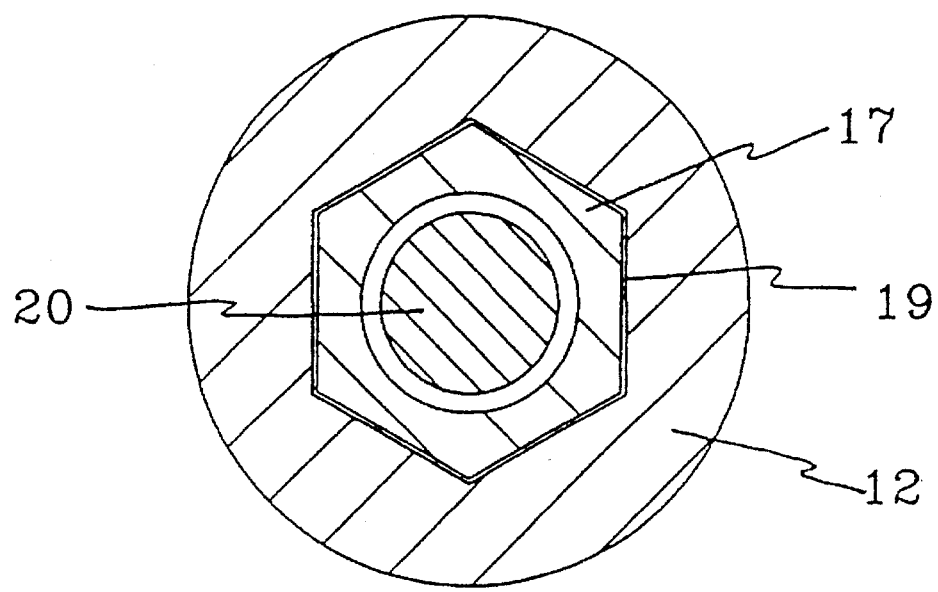
FIG. 3 is a transverse section taken along line 3—3 through the embodiment shown in FIG. 1.

A first preferred embodiment of a dental replacement system 10 in accordance with the invention as shown in FIGS. 1, 2 and 3 includes a transmucosal member or collar 14 fastened to an implant 12 embedded into the jaw bone 13 of a patient, a transmucosal collar 14, and a mounting base 16 for the supporting of an artificial tooth, bridge or denture 18 at a selected orientation different from the longitudinal direction of the implant. The mounting base 16 is functions as a cap for the transmucosal collar 14 to provide a base to which a dental prosthetic structure such as a full or portion denture, an artificial tooth, a dental abutment or an abutment mount can be affixed in a selected orientation irrespective of the longitudinal direction of the implant 12. Thus, the mounting base 16 permits alignment of a dental prosthetic structure affixed thereto with adjacent teeth or abutments irrespective of the orientation of the implant 12. A hex-headed or slotted fixation bolt 20 which extends through a central bore 21 of the transmucosal collar 14 is screwed into the implant 12 and holds the transmucosal collar thereagainst. The transmucosal collar 14 has an annular flange 22 which rests against and is flush with the top end of the implant 12 when the collar is affixed thereto. The annular flange 22 divides the transmucosal collar 14 into a cylindrical, upper attachment portion 15 which extends through the gingival tissue 50 and to which the mounting base is affixed, and a hexagonal, lower portion 17 which extends into a socket 19 of complementary shape in the implant top end 13. This locks the transmucosal collar in the implant 12 against rotation. The mounting base 16 has a cup-shaped body with an end wall 24 having a planar top surface 26 and a cylindrical, depending side wall 28. The top surface 26 is manufactured or machined are an angle to the side wall 28 and, thus, to the longitudinal axis of the base 16. The inner surface of the side wall 28 is provided with a left hand inner thread 30 complementary to a left hand outer thread 32 on the outer surface of the attachment portion 15 of the transmucosal collar 14. Rotation of the mounting base 16 in relation to the transmucosal collar 14 during use of the mounting system is prevented by conventional means well known in the art such as a horizontal worm screw (not illustrated) or one of the adhesives commonly used to prevent screw loosening, for example Omni Lock™. Although the mounting base 16 can be permanently affixed to the transmucosal collar, for improved hygiene and maintenance of the mounting system, the mounting base 16 is releasably affixed to be operator removable. The height of the depending side wall 28 of the mounting base 16 is equal to the height of the attachment portion 15 so that a lower end 36 of the depending side wall engages the flange 22 when the mounting base is fully installed on the transmucosal collar 14. An abutment 38, or an abutment mount 39 in the form of a pin, screw, threaded socket, groove or trench is affixed to or provided in the top surface 26 of the mounting base 16. The abutment 38 is either integral with the mounting base 16, i.e. soldered or cast thereto or affixed to the mounting base by a threaded connection 39. The abutment 38 can also be screwed onto the base 16 and secured thereto by a horizontal worm screw (not shown). A loosening of the fixation bolt 20 during or after installation of the mounting base 16 is prevented, since the hexagonal portion 17 of the transmucosal collar is locked in the implant 12 and the end wall 24 of the base, once installed, rests against the head of the fixation bolt, which together with the opposite direction of the respective threads on the base and the bolt makes rotation of the bolt impossible without removal of the base. The combination of transmucosal collar 14 and mounting base 16 rarely extends above the mucosa. For free standing or single implant bodies such as abutments for partial dentures or single crowns, the mounting base 16 is provided with a square trench 42 (see FIG. 4) which is perfectly mated with a trench (not illustrated) in the threaded attachment portion of the transmucosal collar 14. Thus, a crown's extension into the trenches of the mounting base 16 and the transmucosal collar 14 provides for 100% anti-rotational security.

Figure 4:
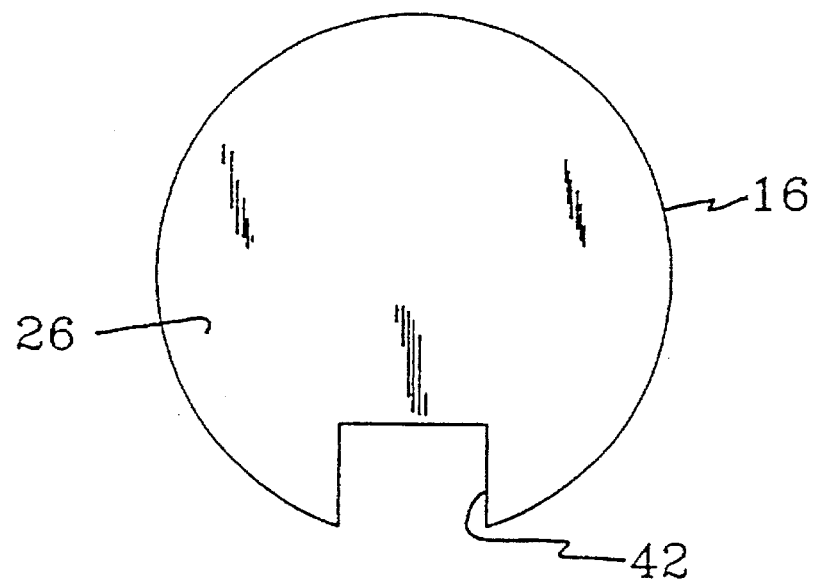
FIG. 4 is a top view of a mounting base of another preferred embodiment.

If the abutment angle which is the angle between an abutment (fixed to the mounting base 16) and the longitudinal axis of the base is so large that the arc described by the abutment tip while screwing of the base onto the transmucosal collar 14 would be too large for the space available between adjacent teeth, the abutment 38 is affixed to the top surface 26 of the base by a threaded precision attachment mount 39 that can be either cast or soldered to the base, at the technician's discretion. For single crowns with poor implant body angle and tight proximity to neighbouring teeth, the top surface 26 of the mounting base 16 can be fitted with a short threaded abutment stud or mount 39 to which the abutment 38 is screwed. A screwed-on abutment can easily be secured against rotation on the base by a horizontal worm screw or square lingual singulum trench 42 through the abutment into the threaded base as shown in FIG. 4. The crown 18 would then extend into this trench making rotation impossible. Abutment loosening can also be prevented by conventional adhesives, such as Omni Lock™. Crowns 18 can be secured to the abutment 38 via a horizontal screw, cement, or other conventional means.

The mounting system of FIGS. 1 and 2 is installed into a patient's mouth by screwing the implant 12 into a hole drilled into the jaw bone 13, after the gingival tissue 50 surrounding the point of insertion of the implant has been folded back by the dental surgeon to expose the jaw bone 13. The transmucosal collar 14 is then inserted with its hexagonal portion 17 into the implant socket 19 until the flange 22 rests against the top end of the implant 12 and subsequently removably affixed to the implant by the fixation bolt 20. Medical silicon is used as a filler for all voids created during installation. The voids are thereby sealed so that a food particle build-up with the resulting embarrassing oral odours is prevented. Subsequently, the mounting base 16 is screwed onto the cylindrical portion 15 of the transmucosal collar 14 and secured with Omni Lock™. The gingival tissue 50 is then placed back over the jaw bone 13 and around the mounting base 16 so that it can heal. The dentist will subsequently take a print of the mounting base 16 which will enable the dental technician to determine the exact angle and location of the base and its top surface 26 so that an abutment or prosthetic structure, for example a crown, can be made for mounting to the base. When the part to be mounted is an abutment, the mounting base 16 is removed for the fastening of the abutment 38 thereto or replacement thereof with an identical base which already has the abutment attached. When the abutment angle is large, the base is provided with an abutment mount 39 to which the abutment is fixed. For single tooth replacement, the artificial tooth or crown is simply modelled after the abutment after an impression has been taken thereof and then placed on the abutment.

Although the preferred outer shape for the mounting base 16 is cylindrical, bases having a square or polygonal outer shape can also be used. Means for fastening the base to the transmucosal collar other than a left hand thread as described above can be used, for example adhesive or a horizontal worm screw. It will be readily apparent to a person skilled in the art of dental replacements that the mounting base and mounting system of the invention can be used for the mounting of permanent replacements such as crowns and bridges as well as removable prosthetic structures such as partial or full dentures. Furthermore, any of the known abutment types used in connection with permanent or removable replacements can be affixed to the attachment base of the invention.

The transmucosal collar 14 can have a threaded cylindrical lower portion which is directly screwed into the implant obviating the use of fixation bolt 20. Although all connections between the implant 12, and the transmucosal collar 14, the collar and the mounting base 16 and the base and the abutment can be made permanent, it is preferred that all these connections are releasable so that all components of the mounting system are operator removable for cleaning and maintenance.

Figure 5:
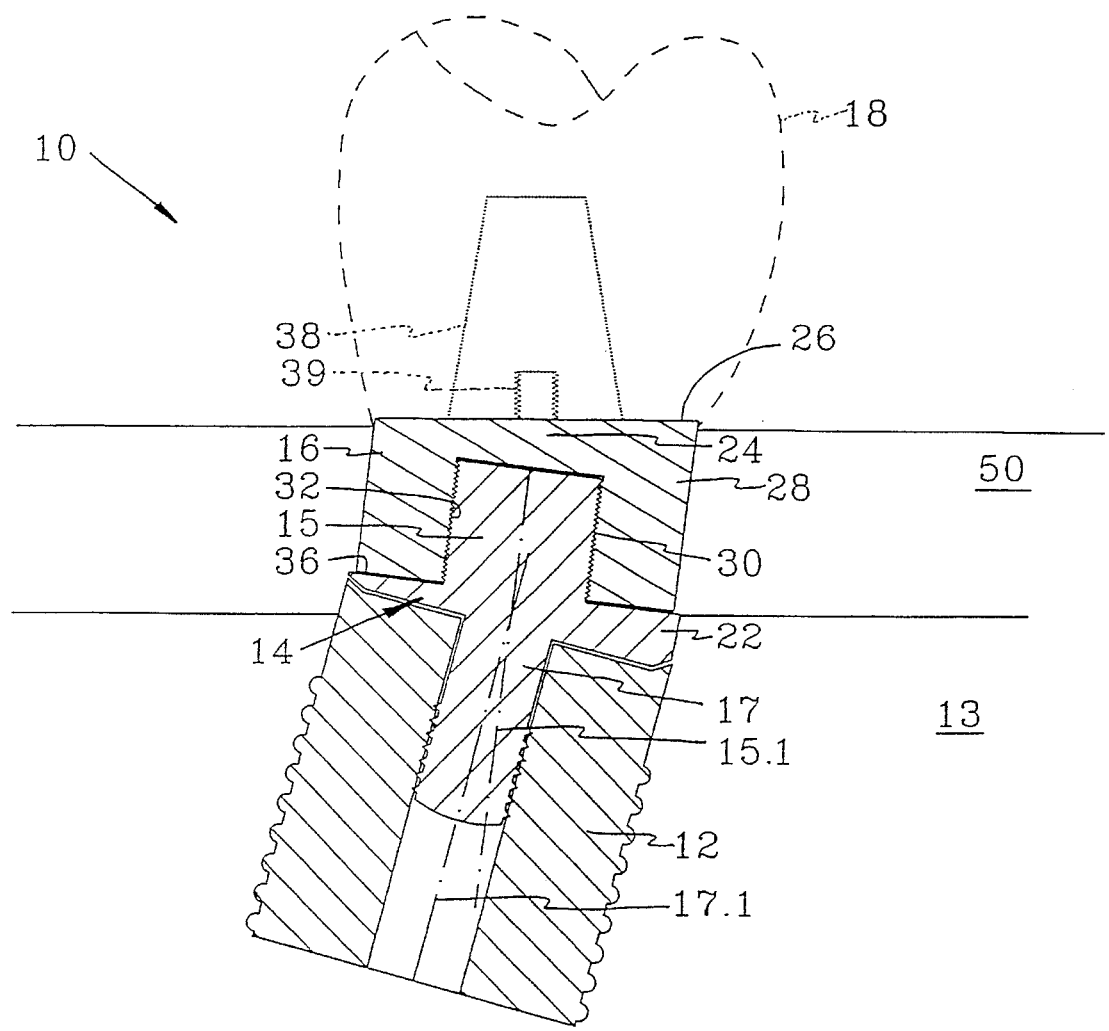
FIG. 5 is a cross-section through a further preferred embodiment wherein the transmucosal member is of an angled configuration.

In the preferred embodiment of the invention illustrated in FIGS. 1 and 2, compensation of implant angulation is possible with a mounting base of angled configuration wherein the top surface 26 is non perpendicular to the side wall 28 or with an abutment 38 or abutment mount 39 which is non perpendicularly affixed to the top surface. However, the present invention provides for compensation of implant angulation at yet another location. As illustrated in FIG. 5, the transmucosal collar 14 in another preferred embodiment is constructed in an angled configuration also referred to as elbow configuration. This is especially advantageous for situations where a dental replacement must be installed in a very confined space and affixed to an implant 12 with a high degree of angulation. In this embodiment, the lower portion 17 of the transmucosal member 14 is in the form of a threaded stud which is screwed directly into the implant 12 and is oriented at an angle to the upper, attachment portion 15 which is constructed the same as in the embodiment of FIGS. 1 and 2. In other words, the axes 15.1, 17.1 of the upper and lower portions 12, 17 respectively extend at an angle to each other. This angle may be selected so that the implant angulation is fully or partly compensated. Since the transmucosal collar 14 must be rotated for screwing into and unscrewing from the implant 12, the angle between the upper and lower portions must be selected in accordance with the spacial constraints of the respective situation so that the upper end of the attachment portion 15 will not come into contact with teeth or abutments directly adjacent the implant during installation of the collar. If the elbow configuration of the transmucosal collar is not sufficient for a complete compensation of implant angulation, either the top surface 26 of the mounting base 16 is cast or machined at an angle to the axis 16.longitudinal of the base or the abutment 38 or abutment mount 39 is affixed at an angle other than perpendicular to the top surface 26, or both. Due to the angled configuration of the transmucosal 14, the annular flange 22 is wedge shaped in cross-section. It becomes apparent that even extreme implant angulations can be compensated with such an embodiment.

The preferred material for the transmucosal collar 14 and the mounting base is titanium. However, if the abutment 38 or abutment mount 39 is affixed by soldering, other precious metals which are more easily soldered are used, for example gold.

Changes and modifications in the specifically described embodiments can be carried out without departing from the scope of the invention which is intended to be limited only by the scope of the appended claims.

The embodiments of the invention in which an exclusive property or privilege is claimed are defined as follows:

1. A mounting system for supporting on a dental endosseous implant having a longitudinal implant axis is in disalignment with the axes of adjacent teeth or abutments, a non-angulated dental abutment for a dental prosthetic structure and in an orientation wherein a longitudinal abutment axis of the abutment intersects the implant axis and coincides with a desired axis which is in alignment with the longitudinal axes of the adjacent teeth or abutments, comprising:

a mounting base having a substantially planar mounting surface for supporting the dental abutment; and a transmucosal member for connecting the mounting base with the dental implant, the transmucosal member including a base portion having means for coaxially engaging the implant and having a first longitudinal axis, and an attachment portion for coaxial engagement with the mounting base and having a second longitudinal axis, and the second longitudinal axis extending at an angle to the first longitudinal axis for partial compensation of the implant angulation; and the mounting base being shaped and constructed such that, when the mounting base is fastened to the implant by way of the transmucosal member, the mounting surface extends at right angles to the desired axis.

2. A mounting system as device in claim 1, further comprising a fastener means for fastening the transmucosal member to the implant.

3. A mounting system as defined in claim 2 wherein the fastener means is a fixation bolt for screwing into the implant and the transmucosal member has a central bore for receiving the fixation bolt.

4. A mounting system as defined in claim 1 further comprising a fastener means for fastening the transmucosal member to the implant, the fastener means being a threaded stud integral with the transmucosal member.

5. A mounting system as defined in claim 1, wherein the mounting system includes a locking means for preventing rotation of the transmucosal member in relation to the implant, the locking means including a socket of non-circular cross-section in a top end of the implant and a protrusion of the transmucosal member which is of the complementary shape to and insertable into the socket.

6. A mounting system as defined in claim 2, wherein the mounting base has an axial recess in a surface substantially opposite the mounting surface for fittingly and coaxially receiving the attachment portion and the fastener means includes an external thread portion on the attachment portion of the transmucosal member and complementary internal thread provided on a side wall of the recess and engageable therewith.

7. A mounting system as defined in claim 6, further including a fixation bolt for connecting the transmucosal member to the implant, the fixation bolt having a right hand thread, the transmucosal member having an axial bore for receiving the fixation bolt, and the interval and external threads being left hand threads to prevent loosening of the fixation bolt when the mounting base is installed on the transmucosal member.

8. A mounting system as defined in claim 1, further comprising an abutment mount permanently affixed to the mounting surface.

9. A mounting system as defined in claim 1, wherein the fastening means is constructed to removably affix the mounting base to the transmucosal member.

10. A mounting system as defined in claim 1, wherein the transmucosal member has an intermediate radially outwardly directed, annular flange which divides the member into the base portion and the attachment portion, the base portion having a hexagonal portion for engagement with a hexagonal socket in a top end of the dental implant, and the attachment portion being cylindrical for engagement with a complementary recess in the mounting base.

\* \* \* \* \*